United States Patent [19]

Beaucage et al.

[11] Patent Number: 5,003,097
[45] Date of Patent: Mar. 26, 1991

[54] METHOD FOR THE SULFURIZATION OF PHOSPHOROUS GROUPS IN COMPOUNDS

[75] Inventors: Serge L. Beaucage, Silver Spring, Md.; Judith B. Regan, Annandale, Va.; Radhakrishnan P. Iyer, Rockville, Md.

[73] Assignee: The United States of America as represented by the Department of Health and Human Services, Washington, D.C.

[21] Appl. No.: 415,710

[22] Filed: Oct. 2, 1989

[51] Int. Cl.$^5$ .................................................. C07F 9/04
[52] U.S. Cl. .................................... 558/129; 530/330; 530/331; 536/22; 536/27; 536/28; 536/29; 548/113; 548/119; 548/413; 548/414; 552/203; 552/209; 562/13; 562/14; 562/15
[58] Field of Search ................. 530/330, 331; 536/22, 536/27, 28, 29; 548/113, 119, 413, 414; 552/203, 209; 558/129; 568/13, 14, 15

[56] References Cited

U.S. PATENT DOCUMENTS 4,415,732 11/1983 Caruthers et al. ..................... 536/29

*Primary Examiner*—Richard L. Raymond
*Attorney, Agent, or Firm*—Birch, Stewart, Kolasch & Birch

[57] ABSTRACT

A method is disclosed for the sulfurization of a phosphorus containing compound, which comprises: solubilizing the phosphorous containing compound and then contacting the phosphorous containing compound, with a sulfur containing compound of the solution formula:

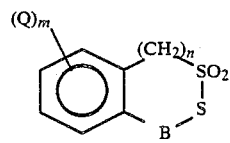

Formula I wherein,
B is selected from the group consisting of —CH$_2$—, —C(O)— or —C(S)—;
Q is a non-interfering moiety or radical; and
m and n, same or different, are selected from the group consisting of zero or one.

11 Claims, No Drawings

METHOD FOR THE SULFURIZATION OF PHOSPHOROUS GROUPS IN COMPOUNDS

BACKGROUND OF THE INVENTION

The present invention provides a method of sulfurizing phosphorus containing compounds, which is reliably useful and which can be used when automating the preparation of such compounds.

The method of the present invention is applicable to a wide variety of compounds, even though it initially grew out of a desire to provide a suitable methodology for the sulfurization of oligonucleotide, which lacked drawbacks associated with other methods generally utilized by those skilled in the art.

The current methodology for the sulfurization of oligonucleotide phosphite triesters via standard "phosphoramidite" chemistry uses a solution of elemental sulfur ($S_8$) in carbon disulfide: pyridine, triethylamine (1:1:0.1 ) (Stec, W. J. et al, J. Am. Chem. Soc. 106, 6077-79, (1984)). The sulfurization reaction with the reagent is slow (ca. 7.5 min) (Stein, C. A. et al, Nucl. Acids Res. 16, 3209-21, (1988)) and because of the insolubility of elemental sulfur in most organic solvents, its precipitation in the delivery lines of commercial instruments, invariably occurs and causes instrument failure. Consequently, the automation of sulfurization reaction with elemental sulfur is erratic and unreliable.

In an attempt to alleviate problems with unreliability and erraticacy, a "nucleoside-H-phosphomate" chemical approach has recently been suggested in the automated preparation of oligonucleotides (Garegg, P. J. et al, Chem. Scripta 28, 280 (1985); Froehler, B. C. et al, Nucl. Acids Res. 14, 5399 (1986)). The method employs sulfurization with elemental sulfur in one step outside the instrument (Froehler, B. C., Tetrahedron Lett. 27, 5565-68 (1986)). Although the automation of the sulfurization reaction is not required with this approach, the "nucleoside-H-phosphomate" methodology suffers from lower stepwise yields (94-96%) during the preparation of synthetic oligomers relative to the "phosphoramidite" approach, which, consistently generates stepwise yields of ca. 99%. This consideration is important especially when large amounts of pure synthetic oligomers are required. Most importantly, the sulfurization of predetermined phosphorus moieties within an oligomer cannot yet be achieved by the "nucleo-H-phosphomate" method.

SUMMARY OF THE INVENTION

One of the objects of the present invention is to provide a method of sulfurizing compounds which can be reliably used in the automated synthesis of desired compounds.

Another of the objects of the present invention is to design and develop sulfurization reagents that will enable reliable automated preparation of specific sulfur-containing oligonucleotides as potential therapeutics against HIV (etiologically, HIV is the virus that causes AIDS in humans) and other viral infections.

Another object of the present invention is to provide appropriate sulfurizing reagents for use in such a method. Requirements for such sulfurizing reagents would include:

(1) solubility of the sulfurization reagents in a variety of organic solvents to prevent precipitation of the reagents in the delivery and/or valve system of the instrument being used, thereby insuring optimal performance of the device during synthesis;

(2) the sulfurizing reagents should be easily handled under normal laboratory conditions and have a reasonable stability in solution for extended periods of time without loss of activity;

(3) the reagents should display rapid sulfurization kinetics so that one may maintain a short synthetic cycle time; and (4) the reagents must selectively and quantitatively react with the phosphorus-containing function of a compound, and in the instance of a phosphorus-containing function of an oligonucleotide, or other similar molecule, must not modify nucleosidic residues so that there is preserved the genetic identity of the macro-molecule.

We have discovered that certain compounds are available which meet all of the above criteria and are thus advantageous to utilize in the automated sulfurization of compounds which contain phosphorous groups, including oligonucleotides.

In view of and in contemplation of the above objects, the present invention provides for the following:

1. A method for the sulfurization of certain phosphorus containing compounds, which comprises the steps of:

Step 1, solubilizing in an aprotic solvent, or a mixture of aprotic solvents, a phosphorous containing compound of the formula:

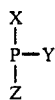     Formula A wherein

X is selected from the group consisting of —$R^1$, —O—$R^1$, —C($R^1$)($R^2$)($R^3$), —NH($R^1$), —N($R^1$)($R^2$) or —S—$R^1$; Y is selected from the group consisting of —$R^2$, —O—$R^2$, —S—$R^2$, —C($R^1$)($R^2$)($R^3$), —NH($R^1$), —N($R^1$)($R^2$), halogen or a protecting group;

Z is selected from the group consisting of —$R^3$, —O—$R^3$, —S—$R^3$, —NH($R^1$) or —N($R^1$)($R^2$); and $R^1$, $R^2$ and $R^3$, same or different, are selected from the group consisting of:

aryl, lower alkyl, cycloalkyl, carbohydrate moieties, glyceride moieties, peptide moieties, nucleotide moieties, amino acid moieties, steroidal moieties, terpene moieties or oligonucleotide moieties; and Step 2, contacting with said phosphorus containing compound in said solution, a compound of the formula:

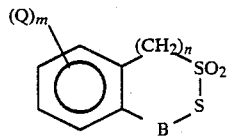     Formula I wherein,

B is selected from the group consisting of —$CH_2$, —C(O)— or —C(S)—;

Q is a non-interfering moiety or radical; and m and n, same or different, are selected from the group consisting of zero or one;

2. A method for the sulfurization of certain phosphorous containing compounds, which comprises the steps of:

Step 1, solubilizing in an aprotic solvent, or a mixture mixture of aprotic solvents, a phosphorous containing compound of the formula:

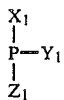

Formula $A_1$ wherein, $X_1$ is selected from the group consisting of $-R^1$, $-O-R^1$, $-S-R^1$, $-C(R^1)(R^2)(R^3)$, $-NH(R^1)$ or $-N(R^1)(R^2)$;

$Y_1$ is selected from the group consisting of $-R^2$, $-O-R^2$, $-S-R^2$, $-C(R^1)(R^2)(R^3)$, $-NH-(R^1)$, $-N(R^1)(R^2)$, halogen or a protecting group;

$Z_1$ is selected from the group consisting of $-R^3$, $-O-R^3$, $-S-R^3$, $-C(R^1)(R^2)(R^3)$, $-NH(R^1)$ or $-N(R^1)(R^2)$; and $R^1$, $R^2$ and $R^3$, same or different, are selected from the group consisting of:

aryl, lower alkyl, cyclo alkyl, carbohydrate moieties, glyceride moieties, peptide moieties, nucleoside moieties, amino acid moieties, steroidal moieties, terpene moieties or oligonucleotide moieties; and Step 2, contacting with said solubilized phosphorous containing compound, a sulfur containing compound of the formula:

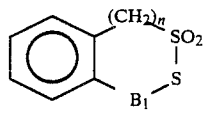

Formula II wherein, $B_1$ is selected from the group consisting of: $-CH_2-$ or $-C(O)-$; and n is selected from the group consisting of zero or one.

3. A method for the sulfurization of certain phosphorous containing compounds, which comprises the steps of:

Step 1, solubilizing in an aprotic solvent, or a mixture of aprotic solvents, a phosphorous containing compound of the formula:

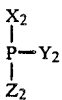

Formula $A_2$ wherein, $X_2$ is selected from the group consisting of $-R^4$, $-O-R^4$, $-S-R^4$, $-C(R^4)(R^5)(R^5)$, $-NH(R^4)$ or $-N(R^4)(R^5)$;

$Y_2$ is selected from the group consisting of $-R^5$, $-O-R^5$, $-S-R^5$, $-C(R^4)(R^5)(R^6)$, $-NH(R^5)$, $-N(R^4)(R^5)$, halogen or a protecting group;

$Z_2$ is selected from the group consisting of $-R^6$, $-O-R^6$, $-S-R^6$, $-C(R^4)(R^5)(R^6)$, $-NH(R^6)$ or $-N(R^4)(R^5)$; and $R^4$, $R^5$ and $R^6$ are selected from the group consisting of: carbohydrate moieties, glyceride moieties and oligonucleotide moieties; and Step 2, contacting with said solubilized phosphorous containing compound, a sulfur containing compound selected from the group consisting of: benzo-2,3-dithian-2,2-dioxide, or 3H-1,2-benzodithiol-3-one-1,1-dioxide.

In order that certain aspects of the present invention will be readily ascertainable and in order to remove any uncertainty which may exist as to the meaning of certain terms used herein, the following glossary of terms is provided.

The term "aprotic solvent" as used herein means such organic solvents as tetrahydrofuran (THF), methylenechloride, dimethylformamide (DMF), and the like. Additionally, a chosen solvent(s) can contain up to 20% V/V of water, if so desired.

The term "mixture of aprotic solvent", as used herein, means a mixture of "aprotic solvents" as defined above. A mixture of aprotic solvents can contain up to 20% V/V of water, if so desired.

The term "aryl" as used herein, means phenyl, benzyl, 1-naphthyl, 2-naphthyl, 2-quinolinyl,isoquinolinyl, 2-, 3-or 4- pyridinyl, and the like.

The term "lower alkyl" as used herein, means an "alkyl" group having 1-8 carbon atoms, which is either branched or straight. Exemplary of such lower alkyl groups are methyl, ethyl, 1-propyl, 2-propyl, 1-butyl, tert-butyl, amyl, isoamyl, hexyl, heptyl and octyl and the like.

The term "cyclo alkyl" as used herein, means a cyclic alkyl radical containing 3-7 atoms. Exemplary of such radicals would be cyclopropyl, cyclohexyl, methylcyclohexyl, and the like.

The term "carbohydrate moieties" as used herein, means polyhydroxy aldehyde radicals, polyhydroxy ketone radicals and other radicals that can be hydrolyzed to the same. Monosaccharidic radicals, disaccharidic radicals and polysaccharidic radicals that may or may not carry specific hydroxy protecting groups, are included within the definition herein employed.

The term "glyceride moiety" as used herein means glycerol radicals that may or may not carry specific hydroxy protecting groups.

The term "peptide moiety" as used herein means amide containing radicals formed by the interaction between amino groups and carboxyl groups of amino acids. The term as utilized herein encompasses dipeptide radicals, tripeptide radicals, and polypeptides up to a molecular weight of 10,000, that may or may not carry specific hydroxy protecting groups.

The term "nucleoside moiety" as used herein, means a radical of a compound formed from a sugar (notably ribose or deoxyribose) with a purine or pyrimidine base by way of an N-glycosyl link. Exemplary of such radicals would be adenosine radicals, cytidine radicals, guanosine radicals, uridine radicals, thymidine radicals, deoxyadenosene radicals, and the like that may or may not carry specific hydroxy protecting groups.

The term "amino acid moiety" as used herein, means amino acid radicals. Exemplary of such radicals would be alanine radicals, valine radicals, glutamine radicals, glycine radicals, histidine radicals, isoleucine radicals, proline radicals, and the like that may or may not carry specific hydroxy protecting groups.

The term "steroidal moieties" as used herein, means radicals of compounds containing a tetracyclyl cyclopenta[a]phenanthrene skeleton. Exemplary of such radicals would be radicals of the following steroids: aldosterone, androsterone, cholecalciferol, cholesterol, choleic acid, corticosterone, cortisol, cortisol acetate, cortisone, cortisone acetate, deoxycorticosterone, ergocalciferol, ergosterol, estradiol-17α, estradiol-17β, estriol, estrone, lanosterol, lithocholic acid, progesterone, testosterone, and the like that may or may not carry specific hydroxy protecting groups.

The term "terpene moiety" as used herein, means radicals of unsaturated hydrocarbons having the formula $C_{10}H_{16}$, which are based upon the isoprene unit $C_5H_8$. Such radicals as encompassed herein, may be acyclics or cyclic with one or more benzenoid groups. Exemplary of such radicals are dipentene radicals, pinene radicals, mysene radicals, menthane radicals, and the like that may or may not carry specific hydroxy protecting groups.

The term "oligonucleotide moiety" as used herein, means a radical containing a minimum of 2 and up to 100 nucleotides. Oligonucleotides disclosed in U.S. Pat. No. 4,415,732 are included within the definition herein employed and U.S. Pat. No. 4,415,732 is hereby incorporated by reference, herein.

The term "nucleotide" as used herein, generally means any compounds containing a heterocyclic compound bound to a phosphorylated sugar by an N-glycosyl link. Exemplary of such compounds are adenosine phosphate, flavin mononucleotide, and the like; but more specifically, the term also encompasses molecules which are combinations of a nucleic acid purine or pyrimidine, one sugar (usually ribose or deoxyribose), and a phosphate group, exemplary of such nucleotides would be adenylic acid, guanylic acid, uridylic acid, cytidylic acid, and the like that may or may not carry specific protecting groups.

The term "non-interfering moiety or radical" as used herein in connection with "Q" in Formula I herein, means any organic radical or moiety of 1-30 atoms which is acyclic, cyclic, or polycyclic, and alkylic or aromatic, and which when substituted on the benzenoid moiety of the compounds of Formula I, does not interfere with the sulfurization of a compound of Formula A, A or Az. Exemplary of such non-interfering moieties are thought to be lower alkyl radicals and phenyl radicals, and other such radicals which are innocuous to the method of the present invention.

DETAILED DESCRIPTION OF THE INVENTION

Having summarized the present invention, the following detailed description is provided to further enable one of ordinary skill in the art to sulfurize phosphorous containing compounds of Formula A, $A_1$ or $A_2$, as provided herein, with compounds encompassed by Formula I or II, as provided herein.

Many important aspects of the present invention are disclosed herein through the use of certain preparations (compounds encompassed by Formula I and II), to sulfurize some representative compounds (oligonucleotides) encompassed by Formulas A, $A_1$ and $A_2$. It is generally thought that the provision of such preparations and their use in the sulfurization of oligonucleotides in the Examples herein, is enabling for one skilled in the art to sulfurize the wide variety of phosphorous containing compounds, herein encompassed. In large part this is due to the ease with which the sulfurization method of the present invention can be carried out, since all compounds encompassed by Formulas I and II herein are thiolsulfonates, which are susceptible to nucleophilic attack at the sulfenyl sulfur leading to cleavage of the polarized bond between the sulfur atoms.

In each of the methods provided herein, the process steps are identical.

The following is a discussion of the reaction steps employed in the sulfurization methods of the present invention. All the methods herein disclosed utilize a two step process.

Step 1-Solubilizing Phosphorous Containing Compounds Encompassed by Formulas A, $A_1$ and $A_2$.

The compounds of Formula A, $A_1$ and $A_2$ encompassed herein need to be solubilized in an aprotic solvent or a mixture of aprotic solvents, before proceeding to step two of the methods herein provided. Most preferably the chosen solvent(s) contains no water, whether they are a single aprotic solvent or a mixture of aprotic solvents. Nonetheless, the method herein disclosed can generally proceed with up to about 20% V/V water in a solvent system, and thus the use of water in amounts up to this percentage is not precluded herein. However, if one does decide to employ water in a solvent system to dissolve a compound encompassed by Formulas A, $A_1$ and $A_2$, it is thought preferable that they employ no more than 10% V/V in the solvent system, even though 20% V/V is allowed.

It is considered herein that one of the most preferred solvent systems to utilize in the present invention is a solvent system consisting essentially of acetonitrile. Even so, other preferred aprotic solvents such as dimethylformamide, methylene chlorine and other halogenated solvents, acetone and mixtures thereof, can also be advantageously used herein.

With regard to an appropriate solvent system temperature for dissolving a compound of Formula A, $A_1$ and $A_2$, it is generally thought that a temperature between $-100°$ C. to $100°$ C. should preferably be used, and even more preferable that a temperature of $-70°$ C. to $+70°$ C. should be used. It is also thought most preferred and advantageous to solubilize a compound of Formula A, $A_1$ and $A_2$ at ambient temperature in an appropriate solvent system, whenever possible.

It is noted that the above temperature ranges are not mandatory, but simply reflect what is thought preferable. Such preferability flows from the fact that such temperature ranges are the preferred temperatures at which to sulfurize compounds of Formula A, $A_1$ and $A_2$ (see Step 2).

Step 2-Contacting a Compound of Formula I or II With a Solubilized Compound from Step 1.

Once one has obtained one of the compounds of Formula I or II, provided herein, the same compound must be placed in contact with the solubilized phosphorous containing compound from Step 1, in order to sulfurize the phosphorous group(s) on such compound. Generally, it is thought advantageous to dissolve the chosen sulfurizing compound of Formula I or II in an aprotic solvent, such as provided above for dissolving compounds of Formula A, $A_1$ and $A_2$ to aid in performing Step 2; but the same is not mandatory and if desired the compound may be added directly to a suitable solvent system containing a compound of Formula A, $A_1$ or $A_2$.

When adding a compound of Formula I or II to a solvent system, it is generally thought preferable that the reaction solvents, and phosphorous containing compound be at a temperature of about −100° C. to +100° C., even more preferably at a temperature of −70° C. to +70° C., and most preferably at an ambient temperature. At any of the above temperatures, sulfurization of the phosphorous group(s) on said compounds occurs relatively spontaneously, and at any of these temperatures, one can expect that sulfurization can occur in a time period of from about 30 seconds to about 1 hour. At ambient temperatures the sulfurization reaction is generally thought to proceed to completion within about 1 minute, when an excess (2–1000, preferably 2–200, molar equivalents relative to phosphorous groups) of a sulfurizing compound (Formula I or II) is utilized. It is noted, that if an excess of a compound of Formula I or II is not used in the method disclosed herein, there should always be present at least an equimolar amount of the same, based on the molar quantity of phosphorous groups one wishes to sulfurize.

With regard to all of the compounds of Formula I or II, provided herein, it is thought that two of the most preferable of these compounds to use in the sulfurization method of the present invention are benzo-2,3-dithian 2,2-dioxide, and 3H-1,2-benzodithiol-3-one 1,1 dioxide. Of these two preferred compounds, it is thought the most preferred one to utilize is 3H-1,2-benzodithiol-3-one 1,1-dioxide.

It is noted that in the method herein disclosed, one may sulfurize more than one phosphorous containing group at a time, on a compound of Formula A, $A_1$ or $A_2$. However, in some instances it is preferable to sulferize phosphorous groups one at a time, in a stepwise manner. One such instance wherein it is preferable to use a stepwise sulfurization process is in the sulfurization of oligonucleotides.

Oligonucleotides are sulferated in a stepwise fashion herein, to prevent cleavage of the oligonucleotide moieties when hydroxy protecting groups are removed of acidolysis therefrom. However, the same should in no way be construed to limit the present invention to only a stepwise sulfurization of compounds encompassed by Formulas A, $A_1$ and $A_2$, which possess multiple phosphorous groups, since presumably many of the compounds encompassed herein, which contain multiple phosphorous groups, can be sulfurized at one time without cleaving or damaging the compound being sulfurized.

Preparation of Sulfurizing Agents.

Several of the compounds encompassed by the Formulas I and II, provided herein, are prepared in the Experimental Section which follows. These compound preparations are considered illustrative of the preparation of other compounds encompassed by Formula I and II herein. This is felt especially true since those of ordinary skill in the art, upon review of the Preparations contained hereinbelow, will readily understand that compounds of Formula I and II can be prepared from known materials with either little or no modification of the synthesis procedure herein disclosed, or by modifying the same in ways apparent to one of ordinary skill in the art.

Of the two preparations provided below for preparing 3H-1,2-benzodithiol-3-one 1,1-dioxide (Preparations 3 and 4), it is thought that the procedure outlined in Preparation 4 is the preferred mode of preparation, inasmuch as less trifluoroacetic acid is required in such a preparation method.

Preparation 1

Preparation of Benzo-2,3-dithian-2,2-dioxide.[1]

To a suspension of o-xylene-$\alpha\alpha'$-dithiol (5 g, 29 mmol) in 40 mL of glacial acetic acid cooled in an ice bath, was added dropwise, over a period of 10 min., 10 mL of 30% hydrogen peroxide (89mmol)[2]. The reaction mixture was stirred at 5° C. for ca. 2 hours and then overnight at ambient temperature. Excess acetic acid was removed under reduced pressure at a temperature lower than 35° C. To the residue was added water (75 ml) and solid sodium bicarbonate until complete neutralization. The mixture was extracted with benzene (ca. 75 mL). The resulting suspension was filtered and the phases separated. The aqueous phase was extracted three more times with benzene, the organic fractions were combined and dried over anhydrous magnesium sulfate. Upon removal of the benzene under reduced pressure, a brown solid was isolated (3.9 g). Recrystallization from chloroform-hexane afforded tan colored crystals.

$^{13}$C NMR (CDCl$_3$): 38.2 ppm (carbon $\alpha$ to the sulfenyl sulfur atom); 61.46 ppm (carbon $\alpha$ to the sulfone function); resonances at 128.2, 128.3, 128.7, 179.7, 130.5 and 130.6 ppm are ascribed to the remaining aromatic carbons. The internal reference is set at 77.0 ppm and corresponds to the middle line of the resonances obtained from the solvent.

Mass spectrometry (e.i., 70e V) : m/z 202 (0.09%) (M+2); 201 (0.1%) (M+1); 200 (0.8%); 135 (100%, base peak); 104 (63%); 78 (28%).

1. A. Luttringhaus and K. Hagele, Angew. Chem. 67, 304 (1955).
2. D. N. Harpp, J. G. Gleason and D. K. Ash, J. Org. Chem. 36, 322–26, (1971).

Preparation 2

Preparation of 3H-1,2-Benzodithiol-3-one.[1]

To a stirred suspension of 2-thiolbenzoic acid (50 g, 0.32 mol) and concentrated sulfuric acid (500 mL) in a three neck round bottom flask (1 L), was added 47 mL of thiolacetic (50 g, 0.66 mol), dropwise over a period of 40 minutes at ambient temperature (water bath). The temperature of the bath was then increased to 50° C. and the brown reaction mixture was stirred for 2 hours. The reaction was stopped by pouring the mixture onto crushed ice (6 L). The precipitate was filtered through a large fritted glass funnel (medium porosity), thoroughly washed with water and suspended in chloroform (300 mL). A saturated solution of sodium bicarbonate (150 mL) was added and the mixture was vigorously shaken and filtered. The solid material isolated was triturated with boiling chloroform (100 mL) and filtered. The trituration process was repeated and the filtrates were combined together. The aqueous phase was separated and the organic phase was extracted once more with a saturated solution of sodium bicarbonate (100 mL) and twice with water (100 mL). The organic layer was then dried over anhydrous magnesium sulfate, filtered and evaporated to dryness under reduced pressure. The yellow material (50.4 g) was dissolved with boiling hexanes (700 mL). The solution was decanted from dark insoluble material, brought to reflux and allowed to cool first at ambient temperature and then kept in the refrigerator (10° C.). The yellow crystals were isolated by filtration, washed with cold hexanes and dried under vacuum. Yield 44.4 g.

$^{13}$C NMR (CDCl$_3$) : 193.5 ppm (carbonyl group); 148.2 ppm (aromatic carbon o to sulphur atom); 129.0 ppm (aromatic carbon α to the carbonyl group); resonances at 133.5, 127.2, 125.6 and 124.6 ppm are ascribed to the remaining aromatic carbons. The internal reference is set at 77.0 ppm and corresponds to the middle line of the resonances obtained from the solvent.

Mass spectrometry (e.i., 70ev) : m/z 170 (M+2) (10%); 169 (M+1) (10%); 168 (100%, base peak); 139 (28%); 104 (33%); 96 (39%); 76 (22%); 69 (21%).

1. M. McKibben and E. W. McClelland, J. Chem. Soc. 170 (1923).

Preparation 3

Preparation of 3H-1,2-Benzodithiol-3-one 1,1-dioxide.[1]

To a stirred suspension of 3H-1,2-Benzodithiol-3-one (44.4 g, 0.26 mole) in trifluoroacetic acid (335 mL) was added dropwise at ambient temperature (water bath), 260 mL of a 3M solution of hydrogen peroxide in trifluoroacetic acid (172 mL of 30% hydrogen peroxide and 328 mL of trifluoroacetic acid)[2] at such a rate, that the temperature of the bath did not exceed 40° C. Once the addition was finished (ca. 90 minutes), the reaction mixture was stirred at 40° C. and the rate of the reaction was monitored by TLC. After 60 minutes under these conditions, 65 mL of the 3M solution of hydrogen peroxide in trifluoroacetic acid was added and the reaction mixture was stirred for an additional 90 minutes. The reaction mixture was filtered and the filtrate was concentrated under reduced pressure to ca. 350 mL. The solution was added onto 3.5 L of crushed ice. The white precipitate was filtered through a 350 mL fritted glass funnel of coarse porosity and thoroughly washed with water until the filtrate was neutral and free of peroxides. The solid material was then transferred into a 500 mL separatory funnel to which was added chloroform (200 mL) and water (100 mL). After vigorous shaking, the organic phase was decanted and dried over anhydrous magnesium sulfate. The solvent was removed under reduced pressure and the amorphous solid was dried under vacuum. The crude compound ((20.8 g) was dissolved in boiling dichloromethane (ca. 70 mL). Hexanes (ca. 50 mL) was added, and the boiling solution was allowed to cool to ambient temperature and then kept in the refrigerator at 10° C. The crystalline material was collected by filtration, washed with cold hexanes and dried under vacuum.

$^{13}$C NMR (CDCl$_3$) 182.9 ppm (carbonyl group); 148.3 ppm (aromatic carbon α to sulphur atom); 130.0 ppm (aromatic carbon α to the carbonyl group); resonances at 136.5, 134.5, 125.6 and 121.9 ppm are ascribed to the remaining aromatic carbons. The internal reference is set at 77.0 ppm and corresponds to the middle line of the resonances obtained from the solvent.

Mass spectrometry (e.i., 70ev): m/z 202 (M+2) (4%); 201 (M+1) (4%); 200 (45%), 136 (100%, base peak); 108 (41%); 104 (37%); 76 (92%); 69 (31%).

1. A. G. Hortmann, A. J. Aron and A. K. Bhattacharya, J. Org. Chem. 43, 3374–78, (1978).
2. C. G. Venier, T. G. Squires, Y-Y Chen, G. P. Hussmann, J. C. Shei and B. F. Smith, J. Org. Chem. 47, 3373–4 (1982).

In order to show the applicability of compounds of Formula I and II in the sulfurization of phosphorous containing compounds encompassed by the Formulas A, A$_1$ and A$_2$ provided herein, the following Examples are provided wherein oligonucleotides are sulfurized. The present invention should not be considered as limited by the same, since the present invention is to be limited only by the scope of the appended claims.

Preparation 4

Preparation of 3H-1,2-Benzodithiol-3-one 1,1-dioxide

To a stirred suspension of 3H-1,2-Benzodithiol-3-one (39.2 g, 0.23 mole) in trifluoroacetic acid (250 mL) was added 40 mL of a 30% aqueous solution of hydrogen peroxide. Cooling was necessary to maintain the internal reaction temperature between 40°–45° C. After 30 minutes, an additional 40 mL of 30% H$_2$O$_2$ was added and the reaction mixture was heated to ensure an internal reaction temperature of 40°–45° C. 30 minutes later, the last portion of 30% H$_2$O$_2$ (40 mL) was added under the same temperature conditions and the rate of the reaction was monitored by TLC (CHCl$_3$) until the disappearance of the slow moving sulfoxide byproduct, i.e., 3H-1,2-benzodithiol-3-one 1-oxide (90 minutes). The reaction mixture was then filtered and the filtrate was added onto 3.5 L of crushed ice. The white precipitate was filtered through a 600 mL fritted glass funnel of coarse porosity and thoroughly washed with water until the filtrate was neutral and free of peroxides. The solid material was then transferred into a 500 mL separatory funnel to which was added dichloromethane (200 mL) and a 1% solution of sodium bisulfite (100 mL). After vigorous shaking, the organic phase was decanted and washed with water (100 mL). The organic layer was dried over anhydrous magnesium sulfate. The solvent was removed under reduced pressure and the amorphous solid was dried under vacuum. The crude compound (20.8 g) was dissolved in boiling dichloromethane (ca. 70 mL). Hexanes (ca. 50 mL) was added, and the boiling solution was allowed to cool to ambient temperature and then kept in the refrigerator at 10° C. The crystalline material was collected by filtration, washed with cold hexanes and dried under vacuum.

$^{13}$C NMR (CDCl$_3$): 182.9 ppm (carbonyl group); 148.3 ppm (aromatic carbon α to the sulphur atom); 130.0 ppm (aromatic carbon α to the carbonyl group); resonances at 136.5, 134.5, 125.6 and 121.9 ppm represent the remaining aromatic carbons. The internal reference is set at 77.0 ppm and corresponds to the middle line of the resonances obtained from the solvent.

Mass spectrometry (70ev): m/z 202 (M+2) (4%); 201 (M+1) (4%); 200 (45%), 136 (100%, base peak); 108 (41%); 104 (37%); 76 (92%); 69 (31%).

EXAMPLE 1

Sulfurization of oligonucleotides.

Certain chemical entities referred to in the present Example are shown in the accompanying Chemical Reaction Schematic for this Example. Certain numbers used herein refer to chemical structures occurring in the same reaction schematic.

The efficacy of one sulfurizing agent of the present invention was tested during the automated preparation of the dinucleotide phosphorothioate 5. A 0.2M solution of the compound of Preparation 3 in acetonitrile was used to sulfurize 4 during a period of 30 s. To assess the extent of the reaction, unreacted 4 was converted to 6 by oxidation with aqueous iodine (Letsinger, R. L. et al, J. Am.Chem. Soc. 98, 3655–3661 (1976)). After standard deprotection (Caruthers, M. H. et al, Gene Amplification and Analysis, Vol. 3, Elsevier, New York, pp. 1–26 (1985)), HPLC analysis of the dimers showed that 7 was generated in greater than 99% yield as a mixture of $R_p$ and $S_p$ diastereoisomers (Stec, W. J. et al, J. Am. Chem. Soc. 106, 6077–6079 (1984)). Less than 1% of the natural phosphodiester was detected. Under similar conditions, an oligodeoxy-nucleotide phosphorothioate (28-mer) complementary to the messenger RNA of the HIV-1 rev gene (Matsukura, M. et al, Proc. Natl. Acad. Sci., U.S.A., 86, 4244–4248 (1989)) was synthesized with a 99% stepwise yield according to "trityl color" determination. $^{31}P$ NMR analysis of the fully deprotected and HPLC-purified oligonucleotide indicated that more than 98% of the resonances observed accounted for P=S($\delta$ 52 ppm) linkages whereas less than 2% of the resonances corresponded to P=O($\delta$ −4 ppm) linkages (Stec, W. J. et al, J. Am. Chem. Soc., 106, 6077–6079 (1984)). To demonstrate the versatility of the synthetic approach, a similar oligomer bearing only two P=S linkages at predetermined positions was also prepared. $^{31}P$ NMR analysis of the purified oligomer displayed the proper P=S resonances in correct integrated ratio relative to the P=O resonances.

Optimum results are thought obtained when the sulfurizing reagent is dissolved in dry acetonitrile prior to use and the solution kept in a dry silanized amber glass bottle that will fit a DNA synthesizer. The glass bottle is silanized by immersion in a 10% solution of dichlorodimethylsilane in dichloromethane for 3-5 minutes. The empty bottle is then rinsed with water and thoroughly dried in an oven at 110° C. We have found that an unsilanized bottle catalysed the decomposition of the sulfurizing reagent within 3-5 days resulting in the formation of a precipitate. Conversely, no precipitation occurred when the reagent is kept in a silanized amber bottle at ambient temperature for as long as one month. Additionally, the reagent retained 95% of its activity after such a long time in solution.

Finally, a random DNA sequence (28-mer; d(TACC-GTAGCTAAGGTCATGCAAGTTCCG)) bearing exclusively P=O linkages and equal number of the four nucleosidic bases was synthesized to investigate potential nucleosidic modification during the sulfurization step. The fully protected oligomer covalently attached to the solid-support was incubated with a 0.2M solution of the compound of Preparation 3 in acetonitrile for 24 hours at ambient temperature. A control experiment in which the protected and support-bound oligomer was incubated in acetonitrile for 24 hours was also performed. After deprotection and purification, the oligomers were subjected to enzymatic degradation with snake venom phosphodiesterase and alkaline phosphatase (Seela, F. et al, Nucl. Acids Res., 15, 3113–3129 (1987)). No evidence of nucleosidic base modification was detected from HPLC analysis of the hydrolysates relative to the control experiment as only peaks corresponding to the four nucleosides were observed.

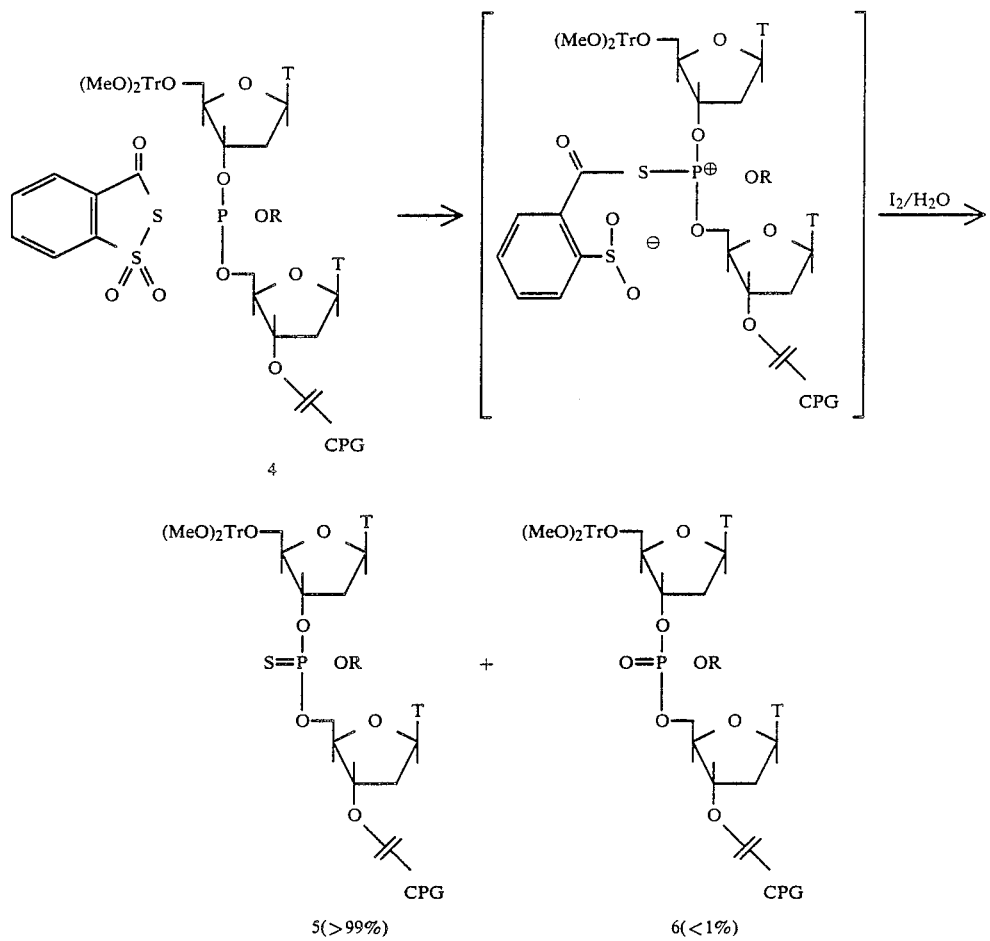

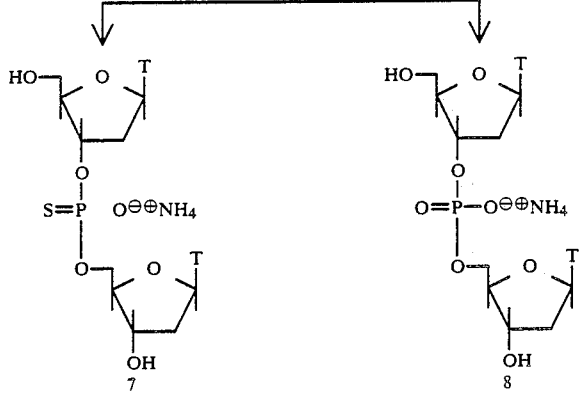

(MeO)₂Tr: di(p-anisyl)phenylmethyl
T: 1-Thyminyl
R: β-cyanoethyl
DCA: dichloroacetic acid
CPG: Controlled-pore glass

EXAMPLE 2

Sulfurization of Phosphorous Containing Oligonucleotides.

When Benzo-2,3-dithian-2,2-dioxide (Preparation is substituted for the compound 3H-1,2-benzodithiol-3-one 1,1-dioxide (Preparation 3) in Example 1, it is expectable that comparable results would be obtained.

EXAMPLE 3

Sulfurization of Phosphorous Containing Compounds found in U.S. Pat. No. 4,415,732.

It is expected that compounds of the Formulas II, III, IIa and IIIa (as occur in U.S. Pat. No. 4,415,732) may be sulfurized by the methods herein disclosed.

More specifically, it is expectable that upon solubilizing a compound of Formula II, IIa, III or IIIa (as found in U.S. Pat. No. 4,415,732) in an aprotic solvent and contacting the same with a compound encompassed by Formula I or II (herein) therein would take place a sulfurization of the phosphorous groups in the former compounds.

The present invention is only limited by the scope of the appended claims.

What is claimed is:

1. A method for the sulfurization of phosphorous containing compounds, which comprises the steps of:

Step 1, solubilizing in an aprotic solvent, or a mixture of aprotic solvents, a phosphorous containing compound of the formula:

Formula A wherein,
X is selected from the group consisting of —R¹, —O—R¹, —C(R¹)(R²)(R³), —NH(R¹), —N(R¹)(R²) or —S—R¹;
Y is selected from the group consisting of —R², —O—R², —S—R⁴, —C(R¹)(R²)(R³), —NH(R¹), —N(R¹)(R²), halogen or a protecting group;
Z is selected from the group consisting of —R³, —O—R³, —S—R³, —NH(R¹) or —N(R¹)(R²); and R¹, R² and R³, same or different, are selected from the group consisting of:
aryl, lower alkyl, cycloalkyl, carbohydrate moieties, glyceride moieties, peptide moieties, nucleotide moieties, amino acid moieties, steroidal moieties, terpene moieties or oligonucleotide moieties;

Step 2, contacting with said phosphorus containing compound in said solution, a sulfur containing compound of the formula

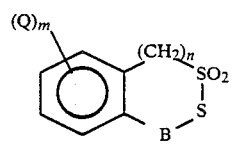

Formula I wherein,
B is selected from the group consisting of —CH₂—, —C(O)— or —C(S)—;
Q is a non-interfering moiety or radical;
m and n, same or different, are selected from the group consisting of zero or one.

2. The method of claim 1, wherein R¹, R²and R³, same or different, are carbohydrate moieties, glyceride moieties or oligonucleotides.

3. The method of claim 2, wherein said compound of Formula I is
benzo-2,3-dithian-2,2-dioxide, or
3H-1,2-benzodithiol-3-one-1,1-dioxide.

4. The method of claim 2, wherein said compound of Formula I is 3H-1,2-benzodithiol-3-one-1,1-dioxide.

5. A method for the sulfurization of phosphorous containing compounds, which comprises the steps of:

Step 1, solubilizing in an aprotic solvent, or a mixture of aprotic solvents, a phosphorous containing compound of the formula:

Formula A₁ wherein,

X₁ is selected from the group consisting of —R¹, —O—R¹, —S—R¹, —C(R¹)(R²)(R³), —NH(R¹) or —N(R¹)(R²);

Y is selected from the group consisting of —R², —O—R², —S—R², —C(R¹)(R²)(R³), —NH—(R¹), —N(R¹)(R²), halogen or a protecting group;

Z₁ is selected from the group consisting of —R³, —O—R³, —S—R³, —C(R¹)(R²)(R³), —NH(R¹) or —N(R¹)(R²);

R¹, R² and R³, same or different, are selected from the group consisting of:

aryl, lower alkyl, cyclo alkyl, carbohydrate moieties, glyceride moieties, peptide moieties, nucleoside moieties, amino acid moieties, steroidal moieties, terpene moieties or oligonucleotide moieties; and Step 2, contacting with said solubilized phosphorous containing compound, a sulfur containing compound of the formula:

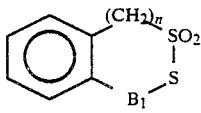

Formula II wherein,

B₁ is selected from the group consisting of: —CH₂— or —C(O)—; and n is selected from the group consisting of zero or one.

6. The method of claim 5, wherein the compound of Formula I is:
benzo-2,3-dithian-2,2-dioxide, or
3H-1,2-benzodithiol-3-one-1,1-dioxide.

7. The method of claim 5, wherein the compound of Formula I is 3H-1,2-benzodithiol-3-one-1,1-dioxide.

8. The method of claim 5, wherein R¹, R² and R³, same or different, are carbohydrate moieties, glyceride moieties or oligonucleotide moieties.

9. The method of claim 8, wherein the compound of Formula I is:
benzo-2,3-dithian-2,2-dioxide or
3H-1,2-benzodithiol-3-one-1,1-dioxide.

10. The method of claim 8, wherein the compound of Formula I is 3H-1,2-benzodithiol-3-one-1,1-dioxide.

11. A method for the sulfurization of certain phosphorous containing compounds, which comprises the steps of:

Step 1, solubilizing in an aprotic solvent, or a mixture of aprotic solvents, a phosphorous containing compound of the formula:

Formula A₂ wherein,

X₂ is selected from the group consisting of —R⁴, —O—R⁴, —S—R⁴, —C(R⁴)(R⁵)(R⁶), —NH(R⁴) or —N(R⁴)(R⁵);

Y₂ is selected from the group consisting of —R⁵, —O—R⁵, —S—R⁵, —C(R⁴)(R⁵)(R⁶), —NH(R⁵), —N(R⁴)(R⁵), halogen or a protecting group;

Z₂ is selected from the group consisting of —R⁶, —O—R⁶, —S—R⁶, —C(R⁴)(R⁵)(R⁶), —NH(R⁶) or —N(R⁴)(R⁵); and R⁴, R⁵ and R⁶ are selected from the group consisting of: carbohydrate moieties, glyceride moieties or oligonucleotide moieties; and Step 2, contacting with said solubilized phosphorous containing compound, a sulfur containing compound selected from the group consisting of:
benzo-2,3-dithian-2,2-dioxide or
3H-1,2-benzodithiol-3-one-1,1-dioxide.

* * * * *